(12) United States Patent
Elder et al.

(10) Patent No.: US 9,645,104 B2
(45) Date of Patent: *May 9, 2017

(54) CAPACITANCE DETECTION IN ELECTROCHEMICAL ASSAY

(71) Applicant: LifeScan Scotland Limited, Inverness (GB)

(72) Inventors: David Elder, Inverness (GB); Sven Rippel, Zwingenberg (GB)

(73) Assignee: LifeScan Scotland Limited, Inverness (GB)

( * ) Notice: Subject to any disclaimer, the term of this patent is extended or adjusted under 35 U.S.C. 154(b) by 406 days.

This patent is subject to a terminal disclaimer.

(21) Appl. No.: 14/246,592

(22) Filed: Apr. 7, 2014

(65) Prior Publication Data

US 2014/0332415 A1    Nov. 13, 2014

Related U.S. Application Data

(62) Division of application No. 13/034,281, filed on Feb. 24, 2011, now abandoned.

(60) Provisional application No. 61/308,167, filed on Feb. 25, 2010.

(51) Int. Cl.
*G01R 27/26* (2006.01)
*G01N 27/30* (2006.01)
*G01N 27/327* (2006.01)
*G01N 27/22* (2006.01)

(52) U.S. Cl.
CPC ....... *G01N 27/307* (2013.01); *G01N 27/3274* (2013.01); *G01N 27/22* (2013.01)

(58) Field of Classification Search
USPC ................................. 324/658–690
See application file for complete search history.

(56) References Cited

U.S. PATENT DOCUMENTS

| 5,372,141 | A | * | 12/1994 | Gallup | ................. | A61B 5/0002 |
| | | | | | | 600/547 |
| 6,179,979 | B1 | | 1/2001 | Hodges et al. | | |
| 6,193,873 | B1 | | 2/2001 | Ohara et al. | | |
| 6,284,125 | B1 | | 9/2001 | Hodges et al. | | |

(Continued)

FOREIGN PATENT DOCUMENTS

| CN | 1412548 A | 4/2003 |
| CN | 1420354 A | 5/2003 |

(Continued)

OTHER PUBLICATIONS

Patent Examination Report No. 1 issued in related Australian Patent Application No. 2011219583, dated Nov. 10, 2014, 3 pages.

(Continued)

*Primary Examiner* — Vincent Q Nguyen

(57) ABSTRACT

A method and system are provided to determine fill sufficiency of a biosensor test chamber by determining capacitance of the test chamber in which an electrochemical reaction is initiated in the test chamber and an oscillating voltage of a predetermined frequency is applied to the chamber. A phase angle between a current output and the oscillating voltage from the chamber is determined and the capacitance is calculated based on a product of the current output and a sine of the phase angle divided by a product of two times pi times the frequency and the voltage.

5 Claims, 11 Drawing Sheets

(56) References Cited

U.S. PATENT DOCUMENTS

| | | | |
|---|---|---|---|
| 6,413,410 | B1 | 7/2002 | Hodges et al. |
| 6,475,372 | B1 | 11/2002 | Ohara et al. |
| 6,716,577 | B1 | 4/2004 | Yu et al. |
| 6,749,887 | B1 | 6/2004 | Dick et al. |
| 6,856,125 | B2 | 2/2005 | Kermani et al. |
| 6,863,801 | B2 | 3/2005 | Hodges et al. |
| 6,872,298 | B2 | 3/2005 | Kermani et al. |
| 6,890,421 | B2 | 5/2005 | Ohara et al. |
| 7,045,046 | B2 | 5/2006 | Chambers et al. |
| 7,195,704 | B2 | 3/2007 | Kermani et al. |
| 7,199,594 | B2 | 4/2007 | Kermani |
| 7,291,256 | B2 | 11/2007 | Teodorczyk et al. |
| 7,498,132 | B2 | 3/2009 | Yu et al. |
| 2003/0094383 | A1 | 5/2003 | Kermani |
| 2003/0098233 | A1 | 5/2003 | Kermani et al. |
| 2003/0109798 | A1 | 6/2003 | Kermani |
| 2003/0160155 | A1 | 8/2003 | Liess |
| 2006/0231418 | A1 | 10/2006 | Harding et al. |
| 2008/0264152 | A1 | 10/2008 | Sullivan |
| 2009/0301899 | A1 | 12/2009 | Hodges et al. |
| 2011/0017592 | A1* | 1/2011 | Nelson ............... G01N 33/5438 204/403.01 |
| 2013/0306492 | A1 | 11/2013 | Iyengar et al. |

FOREIGN PATENT DOCUMENTS

| | | |
|---|---|---|
| CN | 1568452 A | 1/2005 |
| CN | 1646900 A | 7/2005 |
| CN | 101198868 A | 6/2008 |
| EP | 2138841 A2 | 12/2009 |
| JP | S59187272 A | 10/1984 |
| JP | H01110267 A | 4/1989 |
| JP | 2003240747 A | 8/2003 |
| JP | 2003247966 A | 9/2003 |
| JP | 2005518527 A | 6/2005 |
| JP | 2009222433 A | 10/2009 |
| WO | WO 03/069304 A2 | 8/2003 |
| WO | WO 2005/003748 A1 | 1/2005 |
| WO | WO 2008/051804 A2 | 5/2008 |

OTHER PUBLICATIONS

Patent Examination Report No. 1 issued in related Australian Patent Application No. 2011360140, dated Jan. 31, 2014, 2 pages.
Patent Examination Report No. 1 issued in related Australian Patent Application No. 2011360141, dated Jan. 9, 2015, 3 pages.
First Office Action issued in related Chinese Patent Application No. 201180068457.0, dated Jul. 31, 2014, 12 pages.
Search Report issued in related Chinese Patent Application No. 201180068457.0, dated Jul. 14, 2014, 2 pages.
European Search Report issued in related European Patent Application No. 14157379.0, dated Aug. 1, 2014, 4 pages.
International Preliminary Report on Patentability and Written Opinion issued in related International Application No. PCT/GB2011/001211, Feb. 24, 2011, 8 pages.
International Search Report and Written Opinion issued in related International Application No. PCT/GB2011/001210 Dec. 6, 2011, 9 pages.
Search Report issued in related Chinese Patent Application No. 201180010911.7, Nov. 11, 2013, 2 pages.
First Office Action issued in related Chinese Patent Application No. 201180010911.7, Nov. 19, 2013, 10 pages.
Supplemental Search Report issued in related Chinese Patent Application No. 201180010911.7, Jun. 17, 2014, 2 pages.
Second Office Action issued in related Chinese Patent Application No. 201180010911.7, Jun. 30, 2014, 9 pages.
European Search Report issued in related European Patent Application No. 14152014.8, May 30, 2014, 8 pages.
Notice of Reasons for Rejection issued in related Japanese Patent Application No. 2012-554409, Jun. 3, 2014.
International Application No. PCT/GB2011/000267, Invitation to Pay Additional Fees and, Where Applicable, Protest Fees Dated Jun. 7, 2011, 5 pages, European Patent Office, Rijswijk, Netherlands.
International Search Report for PCT/GB2011/000267, 17 pages, dated Sep. 29, 2011.
Bissi, L., et al., "Smart Capacitive Biosensor Based on a Programmable System-on-Chip, Featuring a Novel Method of Improving the Performance of its Analog Blocks", IEEE International Instrumentation and Measurement Technology Conference, Victoria, Vancouver Island, Canada, May 12-15, 2008, 5 pages.
PCT Search Report, International Application No. PCT/GB2011/001211 dated Mar. 20, 2012, 4 pages.
International Search Report for PCT/GB2011/001211, 8 pages, dated Sep. 6, 2013.
International Application PCT/GB2011/001210, PCT Preliminary Report and Opinion, 6 pages, dated Sep. 6, 2013.
China Patent Application No. 201180010911.7, First Office Action, 4 pages, Nov. 19, 2013.
Office Action issued in related Russian Application No. 2013143163, dated Feb. 9, 2015, 15 pages.

* cited by examiner

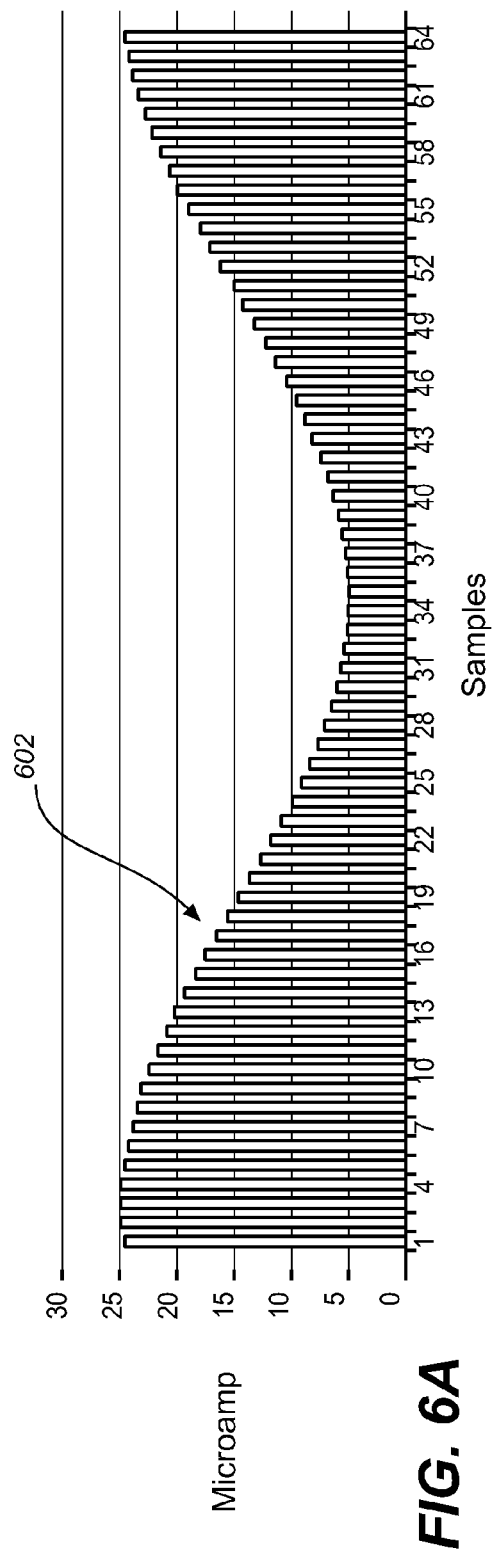
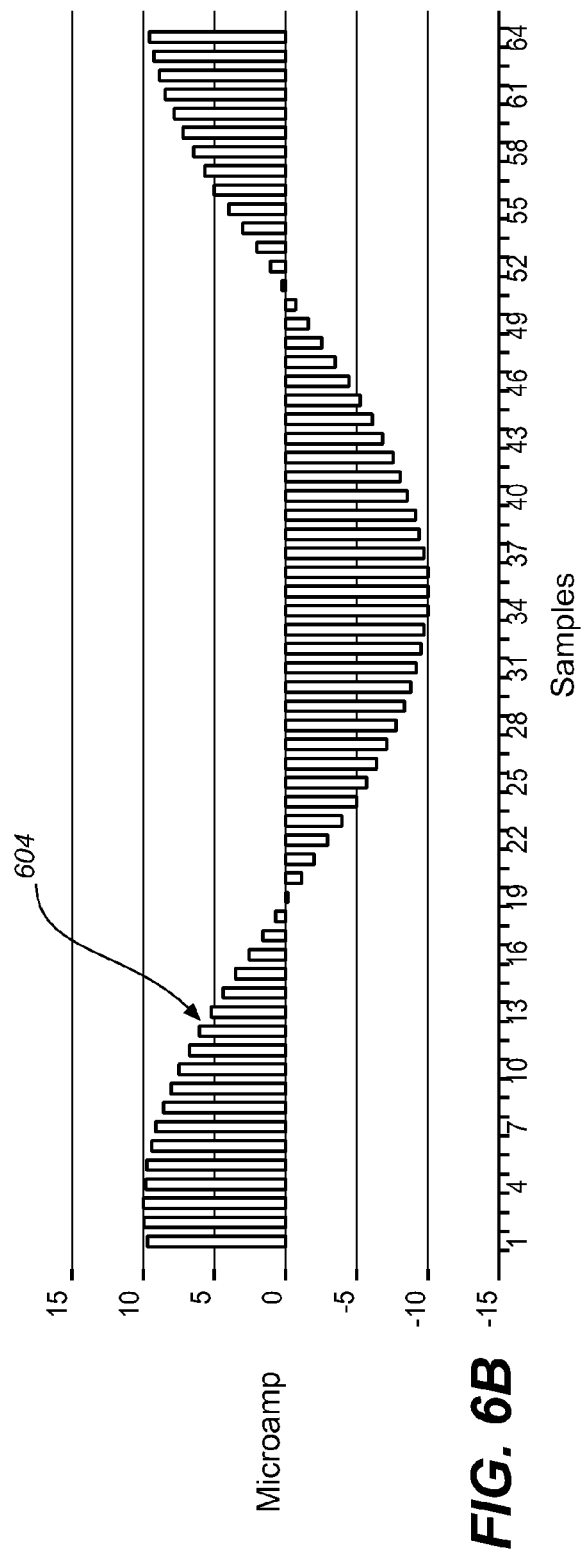
FIG. 6A
FIG. 6B

FIG. 6C
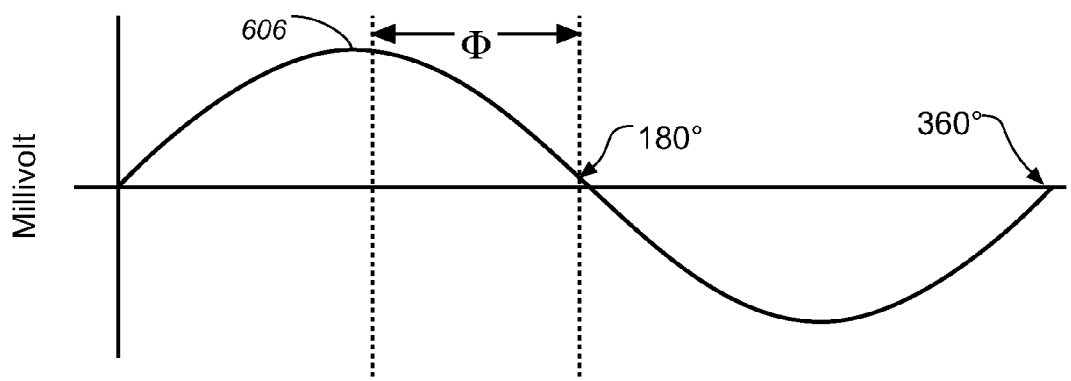
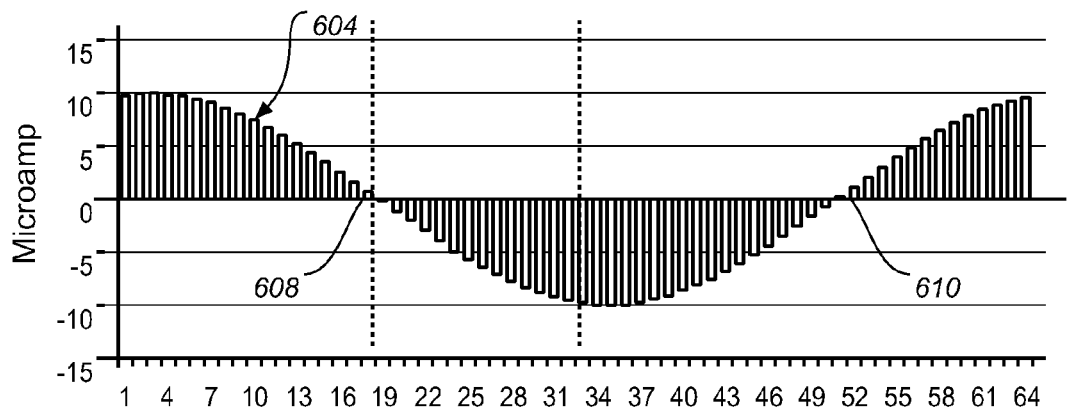
FIG. 6D
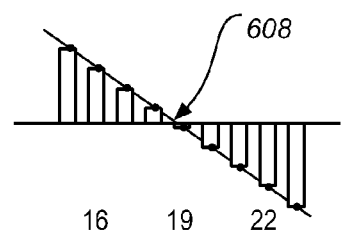
FIG. 6E

Parallel R-C Model of Test Chamber

Phasor Diagram

CAPACITANCE DETECTION IN ELECTROCHEMICAL ASSAY

PRIORITY

This DIVISIONAL application claims the benefits of priority under 35 USC §§120 and 121 from prior filed U.S. patent application Ser. No. 13/034,281 filed on Feb. 24, 2011, pending, which prior filed application (Ser. No. 13/034,281) claims the benefits of priority under 35 USC §119 from prior filed U.S. Provisional Application Ser. No. 61/308,167 filed on Feb. 25, 2010, in which all prior filed applications are incorporated by reference in their entirety into this application.

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a sample-receiving chamber in an electrochemical cell that includes two electrodes, e.g., a counter and working electrode. The analyte is allowed to react with a redox reagent to form an oxidizable (or reducible) substance in an amount corresponding to the analyte concentration. The quantity of the oxidizable (or reducible) substance present is then estimated electrochemically and related to the amount of analyte present in the initial sample.

Such systems are susceptible to various modes of inefficiency and/or error. For example, variations in temperatures can affect the results of the method. This is especially relevant when the method is carried out in an uncontrolled environment, as is often the case in home applications or in third world countries. Errors can also occur when the sample size is insufficient to get an accurate result. Partially filled test strips can potentially give an inaccurate result because the measured test currents are proportional to the area of the working electrode that is wetted with sample. Thus, partially filled test strips can under certain conditions provide a glucose concentration that is negatively biased.

SUMMARY OF THE DISCLOSURE

Applicants believe that effects of parallel strip resistance in determining filled biosensor test strips have been ignored, leading to inaccurate high measurement of capacitance in a test strip, especially when lower parallel resistance is encountered. Exemplary embodiments of applicants' invention take into consideration this effect and at the same time obviate the need to determine the resistance in a biosensor test chamber.

In one aspect, a method of determining capacitance of a biosensor is provided. The biosensor includes a chamber having two electrodes disposed in the chamber and coupled to a microcontroller. The method can be achieved by: initiating an electrochemical reaction in the biosensor chamber; applying an oscillating voltage of a predetermined frequency to the chamber; determining a phase angle between a current output and the oscillating voltage from the chamber; and calculating a capacitance of the chamber based on a product of the current output and a sine of the phase angle divided by a product of two times pi times the frequency and the voltage.

In a further aspect, an analyte measurement system is provided that includes an analyte test strip and analyte test meter. The analyte test strip includes a substrate having a reagent disposed thereon, and at least two electrodes proximate the reagent in test chamber. The analyte meter includes a strip port connector disposed to connect to the two electrodes, a power supply, and a microcontroller electrically coupled to the strip port connector and the power supply. The microcontroller is programmed to: initiate an electrochemical reaction in the biosensor chamber; apply an oscillating voltage of a predetermined frequency to the chamber; determine a phase angle between a current output and the oscillating voltage from the chamber; and calculate a capacitance of the chamber based on a product of the current output and a sine of the phase angle divided by a product of two times pi times the frequency and the voltage.

In yet another aspect, analyte measurement system is provided that includes an analyte test strip and analyte test meter. The test strip includes a substrate having a reagent disposed thereon, and at least two electrodes proximate the reagent in test chamber. The analyte meter includes a strip port connector disposed to connect to the two electrodes, a power supply, and a microcontroller electrically coupled to the strip port connector and the power supply such that a percent error in capacitance measurement of the test strip across a range of capacitance as compared to a referential parallel R-C circuit is less than about 3%.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE FIGURES

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 6A illustrates a sampling of the current output indicated at area 602.

FIG. 6B illustrates the alternating current output once the direct-current component has been removed from the sampled data of FIG. 6A.

FIGS. 6C and 6D illustrate the phase angle between the alternating voltage applied to the test strip and the alternating current output from the test strip.

FIG. 6E illustrates an interpolation of the sampled data to determine the cross-over point of FIG. 6D for comparison with the cross-over point of the applied current of FIG. 6C.

DETAILED DESCRIPTION OF THE EXEMPLARY FIGURES

Figure 1:
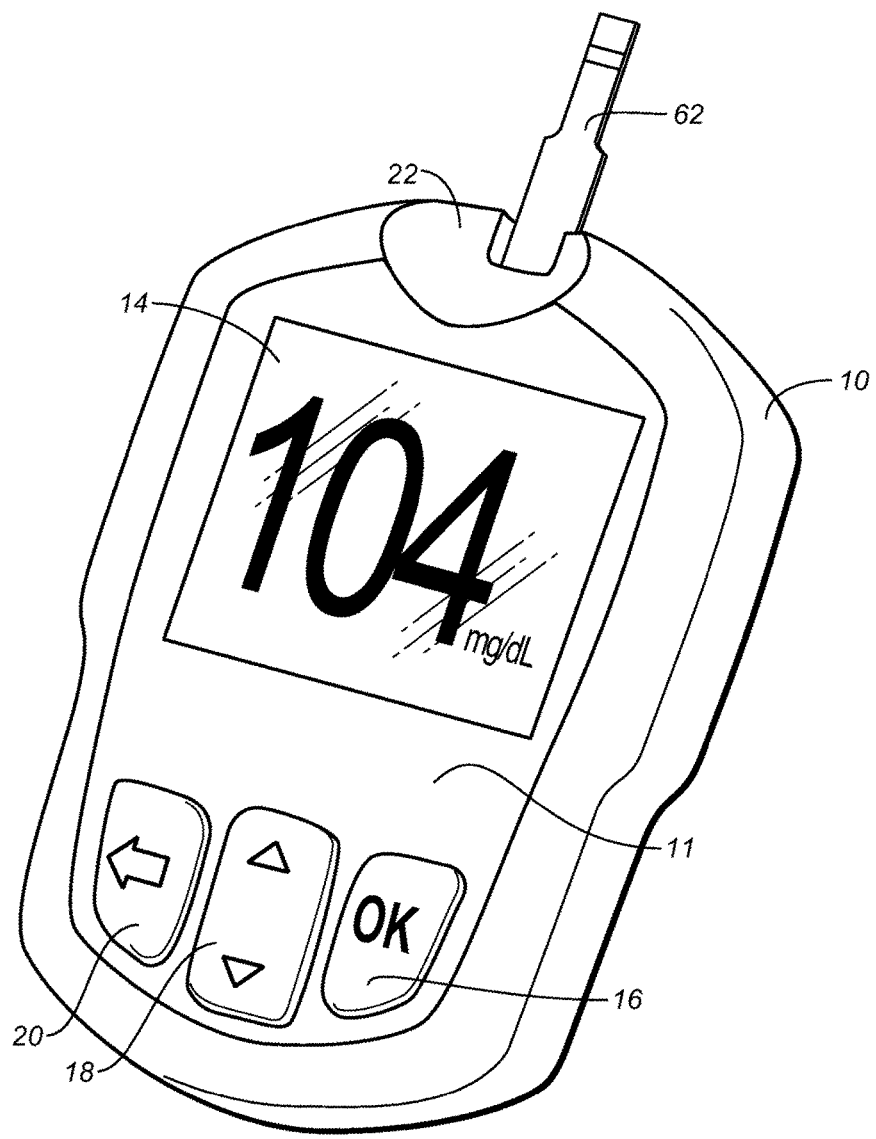
FIG. 1 illustrates an exemplary analyte measurement system including an analyte test meter and test strip.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

The subject systems and methods are suitable for use in the determination of a wide variety of analytes in a wide variety of samples, and are particularly suited for use in the determination of analytes in whole blood, plasma, serum, interstitial fluid, or derivatives thereof. In an exemplary embodiment, a glucose test system based on a thin-layer cell design with opposing electrodes and tri-pulse electrochemical detection that is fast (e.g., about 5 second analysis time), requires a small sample (e.g., about 0.4 µL (microliter)), and can provide improved reliability and accuracy of blood glucose measurements. In the reaction cell, glucose in the sample can be oxidized to gluconolactone using glucose dehydrogenase and an electrochemically active mediator can be used to shuttle electrons from the enzyme to a working electrode. A potentiostat can be utilized to apply a tri-pulse potential waveform to the working and counter electrodes, resulting in test current transients used to calculate the glucose concentration. Further, additional information gained from the test current transients may be used to discriminate between sample matrices and correct for variability in blood samples due to hematocrit, temperature variation, electrochemically active components, and identify possible system errors.

The subject methods can be used, in principle, with any type of electrochemical cell having spaced apart first and second electrodes and a reagent layer. For example, an electrochemical cell can be in the form of a test strip. In one aspect, the test strip may include two opposing electrodes separated by a thin spacer for defining a sample-receiving chamber or zone in which a reagent layer is located. One skilled in the art will appreciate that other types of test strips, including, for example, test strips with co-planar electrodes may also be used with the methods described herein.

FIG. 1 illustrates a diabetes management system that includes a diabetes data management unit 10 and a biosensor in the form of a glucose test strip 80. Note that the diabetes data management unit (DMU) may be referred to as an analyte measurement and management unit, a glucose meter, a meter, and an analyte measurement device. In an embodiment, the DMU may be combined with an insulin delivery device, an additional analyte testing device, and a drug delivery device. The DMU may be connected to the computer 26 or server 70 via a cable or a suitable wireless technology such as, for example, GSM, CDMA, BlueTooth, WiFi and the like.

Referring back to FIG. 1, glucose meter 10 can include a housing 11, user interface buttons (16, 18, and 20), a display 14, and a strip port opening 22. User interface buttons (16, 18, and 20) can be configured to allow the entry of data, navigation of menus, and execution of commands. User interface button 18 can be in the form of a two way toggle switch. Data can include values representative of analyte concentration, and/or information, which are related to the everyday lifestyle of an individual. Information, which is related to the everyday lifestyle, can include food intake, medication use, occurrence of health check-ups, and general health condition and exercise levels of an individual.

Figure 2:
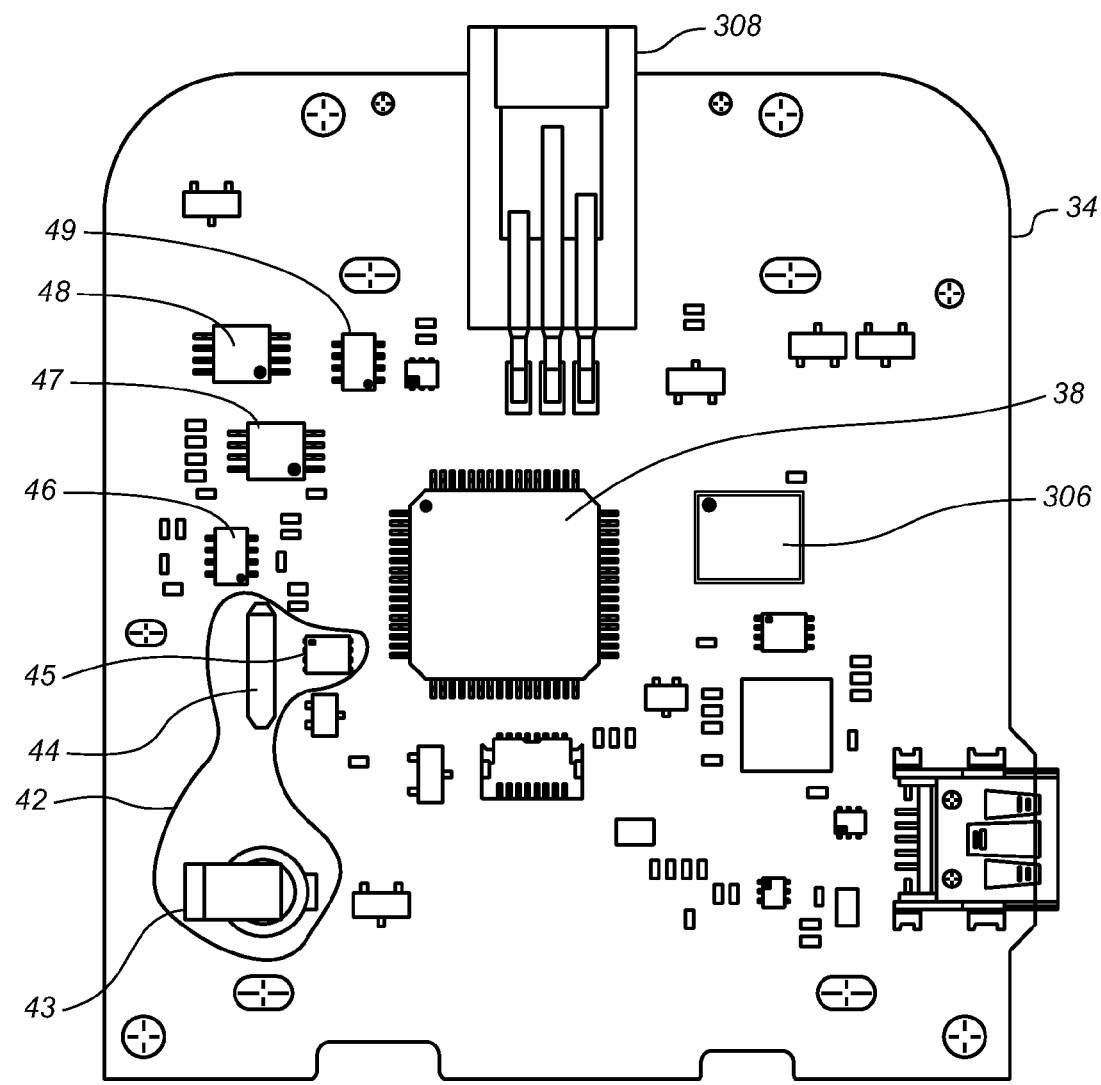
FIG. 2 illustrates in simplified schematic view of an exemplary circuit board for the meter of FIG. 1.

The electronic components of meter 10 can be disposed on a circuit board 34 that is within housing 11. FIG. 2 illustrates (in simplified schematic form) the electronic components disposed on a top surface of circuit board 34. On the top surface, the electronic components may include a strip port opening 308, a microcontroller 38, a non-volatile flash memory 306, a data port 13, a real time clock 42, and a plurality of operational amplifiers (46-49). On the bottom surface, the electronic components may include a plurality of analog switches, a backlight driver, and an electrically erasable programmable read-only memory (EEPROM, not shown). Microcontroller 38 can be electrically connected to strip port opening 308, non-volatile flash memory 306, data port 13, real time clock 42, the plurality of operational amplifiers (46-49), the plurality of analog switches, the backlight driver, and the EEPROM.

Referring back to FIG. 2, the plurality of operational amplifiers can include gain stage operational amplifiers (46 and 47), a trans-impedance operational amplifier 48, and a bias driver operational amplifier 49. The plurality of operational amplifiers can be configured to provide a portion of the potentiostat function and the current measurement function. The potentiostat function can refer to the application of a test voltage between at least two electrodes of a test strip. The current function can refer to the measurement of a test current resulting from the applied test voltage. The current measurement may be performed with a current-to-voltage converter. Microcontroller 38 can be in the form of a mixed signal microprocessor (MSP) such as, for example, the Texas Instrument MSP 430. The MSP 430 can be configured to also perform a portion of the potentiostat function and the current measurement function. In addition, the MSP 430 can also include volatile and non-volatile memory. In another embodiment, many of the electronic components can be integrated with the microcontroller in the form of an application specific integrated circuit (ASIC).

Strip port connector 308 can be located proximate the strip port opening 22 and configured to form an electrical connection to the test strip. Display 14 can be in the form of a liquid crystal display for reporting measured glucose levels, and for facilitating entry of lifestyle related information. Display 14 can optionally include a backlight. Data port 13 can accept a suitable connector attached to a connecting lead, thereby allowing glucose meter 10 to be linked to an external device such as a personal computer. Data port 13 can be any port that allows for transmission of data such as, for example, a serial, USB, or a parallel port.

Real time clock 42 can be configured to keep current time related to the geographic region in which the user is located and also for measuring time. Real time clock 42 may include a clock circuit 45, a crystal 44, and a super capacitor 43. The DMU can be configured to be electrically connected to a power supply such as, for example, a battery. The super capacitor 43 can be configured to provide power for a prolonged period of time to power real time clock 42 in case there is an interruption in the power supply. Thus, when a battery discharges or is replaced, real time clock does not have to be re-set by the user to a proper time. The use of real time clock 42 with super capacitor 43 can mitigate the risk that a user may re-set real time clock 42 incorrectly.

Figure 3:
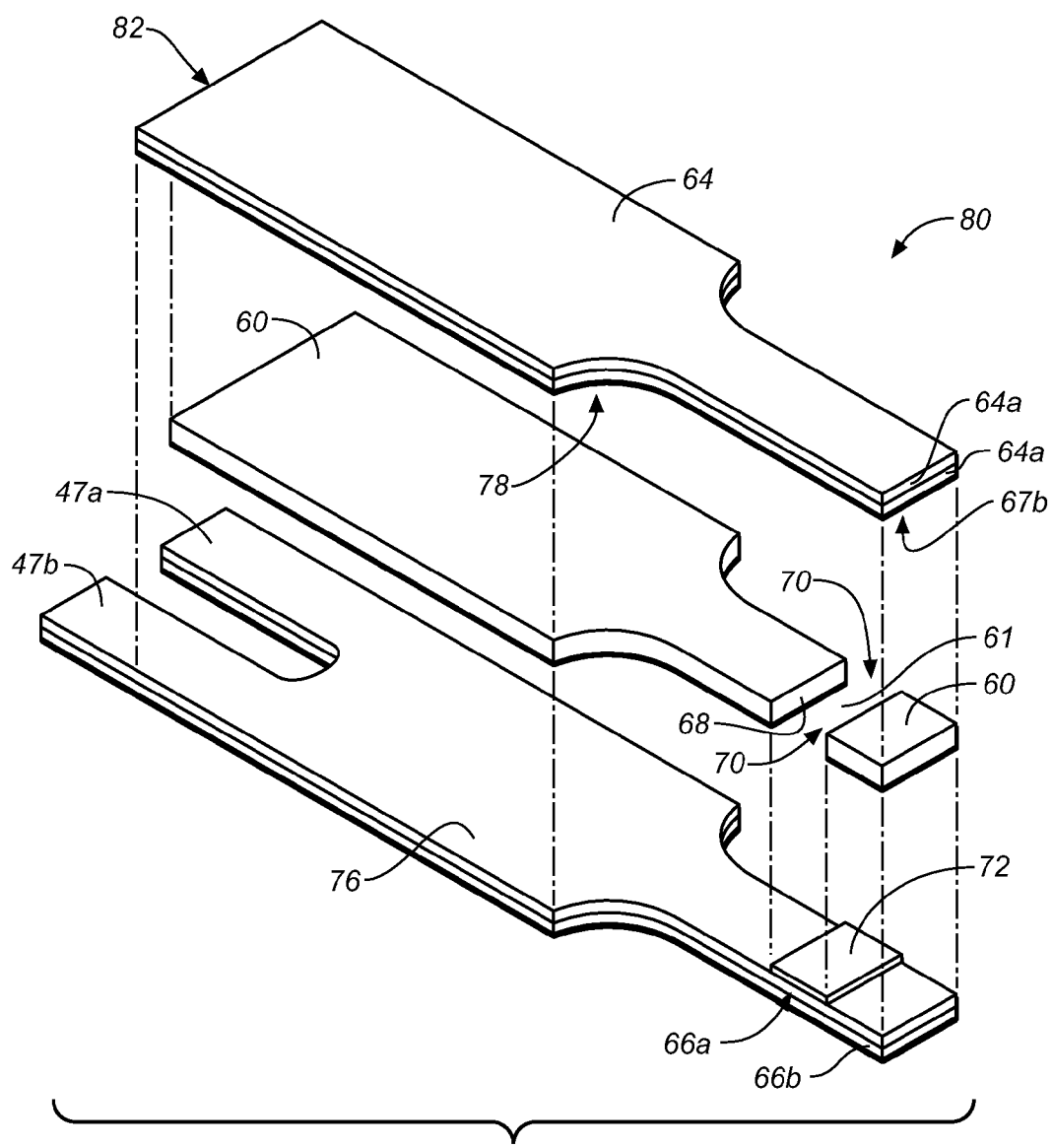
FIG. 3 illustrates an exploded perspective view of the test strip of FIG. 1.
Figure 4:
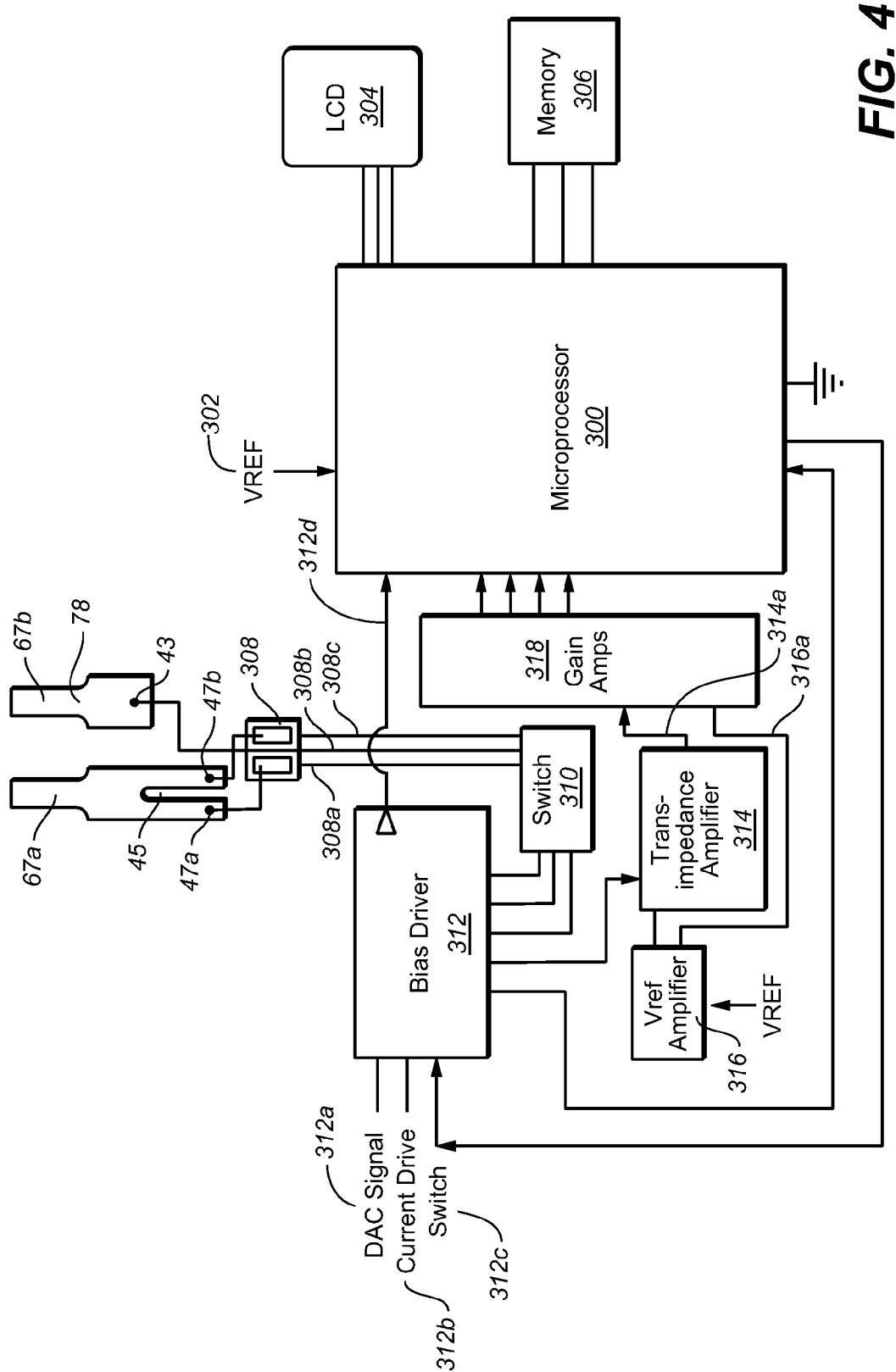
FIG. 4 illustrates a simplified schematic of the components to determine capacitance of a filled test strip.

FIG. 3 illustrates an exemplary test strip 80, which includes an elongate body extending from a distal end 80 to a proximal end 82, and having lateral edges. As shown here, the test strip 80 also includes a first electrode layer 66a, insulation layer 66b, a second electrode layer 64a, insulation layer 64b, and a spacer 60 sandwiched in between the two electrode layers 64a and 66a. The first electrode layer 66a can include a first electrode 67a, a first connection track 76, and a first contact pad 47, where the first connection track 76 electrically connects the first electrode layer 66a to the first contact pad 67, as shown in FIGS. 3 and 4. Note that the first electrode 67a is a portion of the first electrode layer 66a that is immediately underneath the reagent layer 72. Similarly, the second electrode layer 64a can include a second electrode 67b, a second connection track 78, and a second contact pad 78, where the second connection track 78 electrically connects the second electrode 67b with the second contact pad 78, as shown in FIGS. 3 and 4. Note that the second electrode includes a portion of the second electrode layer 64a that is above the reagent layer 72.

As shown in FIG. 3, the sample-receiving chamber 61 is defined by the first electrode, the second electrode, and the spacer 60 near the distal end 80 of the test strip 80. The first electrode 67a and the second electrode 67b can define the bottom and the top of sample-receiving chamber 61, respectively. A cutout area 68 of the spacer 60 can define the sidewalls of the sample-receiving chamber 61. In one aspect, the sample-receiving chamber 61 can include ports 70 that provide a sample inlet and/or a vent. For example, one of the ports can allow a fluid sample to ingress and the other port can allow air to egress. In one exemplary embodiment, the first electrode layer 66a and the second electrode layer 64a can be made from sputtered palladium and sputtered gold, respectively. Suitable materials that can be employed as spacer 60 include a variety of insulating materials, such as, for example, plastics (e.g., PET, PETG, polyimide, polycarbonate, polystyrene), silicon, ceramic, glass, adhesives, and combinations thereof. In one embodiment, the spacer 60 may be in the form of a double sided adhesive coated on opposing sides of a polyester sheet where the adhesive may be pressure sensitive or heat activated.

Referring back to FIG. 3, the area of first electrode and second electrode can be defined by the two lateral edges and cutout area 68. Note that the area can be defined as the surface of the electrode layer that is wetted by liquid sample. In an embodiment, the adhesive portion of spacer 60 can intermingle and/or partially dissolve the reagent layer so that the adhesive forms a bond to the first electrode layer 66A. Such an adhesive bond helps define the portion of the electrode layer that can be wetted by liquid sample and also electrooxidize or electroreduce mediator.

Either the first electrode or the second electrode can perform the function of a working electrode depending on the magnitude and/or polarity of the applied test voltage. The working electrode may measure a limiting test current that is proportional to the reduced mediator concentration. For example, if the current limiting species is a reduced mediator (e.g., ferrocyanide), then it can be oxidized at the first electrode as long as the test voltage is sufficiently less than the redox mediator potential with respect to the second electrode. In such a situation, the first electrode performs the function of the working electrode and the second electrode performs the function of a counter/reference electrode. Note that one skilled in the art may refer to a counter/reference electrode simply as a reference electrode or a counter electrode. A limiting oxidation occurs when all reduced mediator has been depleted at the working electrode surface such that the measured oxidation current is proportional to the flux of reduced mediator diffusing from the bulk solution towards the working electrode surface. The term bulk solution refers to a portion of the solution sufficiently far away from the working electrode where the reduced mediator is not located within a depletion zone. It should be noted that unless otherwise stated for test strip 80, all potentials applied by test meter 10 will hereinafter be stated with respect to second electrode. Similarly, if the test voltage is sufficiently greater than the redox mediator potential, then the reduced mediator can be oxidized at the second electrode as a limiting current. In such a situation, the second electrode performs the function of the working electrode and the first electrode performs the function of the counter/reference electrode. Details regarding the exemplary test strip, operation of the strip and the test meter are found in U.S. Patent Application Publication No. 20090301899, which is incorporated by reference in its entirety herein, with a copy attached to the Appendix.

Referring to FIG. 3, test strip 80 can include one or more working electrodes and a counter electrode. Test strip 80 can also include a plurality of electrical contact pads, where each electrode can be in electrical communication with at least one electrical contact pad. Strip port connector 308 can be configured to electrically interface to the electrical contact pads and form electrical communication with the electrodes. Test strip 80 can include a reagent layer that is disposed over at least one electrode. The reagent layer can include an enzyme and a mediator. Exemplary enzymes suitable for use in the reagent layer include glucose oxidase, glucose dehydrogenase (with pyrroloquinoline quinone co-factor, "PQQ"), and glucose dehydrogenase (with flavin adenine dinucleotide co-factor, "FAD"). An exemplary mediator suitable for use in the reagent layer includes ferricyanide, which in this case is in the oxidized form. The reagent layer can be configured to physically transform glucose into an enzymatic by-product and in the process generate an amount of reduced mediator (e.g., ferrocyanide) that is proportional to the glucose concentration. The working electrode can then measure a concentration of the reduced mediator in the form of a current. In turn, glucose meter 10 can convert the current magnitude into a glucose concentration. Details of the preferred test strip are provided in U.S. Pat. Nos.

6,179,979; 6,193,873; 6284125; 6413410; 6475372; 6716577; 6749887; 6863801; 6890421; 7045046; 7291256; 7498132, all of which are incorporated by reference in their entireties herein.

FIG. 4 illustrates, in simplified schematic form, of various functional components utilized for capacitance determination. In particular, the components include a microcontroller 300. A preferred embodiment of the microcontroller 300 is available from Texas Instrument as ultra-low power microcontroller model MSP 430. Microcontroller ("MC") 300 may be provided with DAC output and built-in A-D conversion. MC 300 is suitably connected to a LCD screen 304 to provide a display of the test results or other information related to the test results. Memory 306 is electrically connected to the MC 300 for storage of test results, sensed current and other necessary information or data. The test strip may be coupled for a test measurement via a strip port connector ("SPC") 308. SPC 308 allows the test strip to interface with MC 300 via a first contact pad 47a, 47b and a second contact pad 43. The second contact pad 43 can be used to establish an electrical connection to the test meter through a U-shaped notch 45, as illustrated in FIG. 4. SPC 308 may also be provided with electrode connectors 308a and 308c. The first contact pad 47 can include two prongs denoted as 47a and 47b. In one exemplary embodiment, the first electrode connectors 308a and 308c separately connect to prongs 47a and 47b, respectively. The second electrode connector 308b can connect to second contact pad 43. The test meter 10 can measure the resistance or electrical continuity between the prongs 47a and 47b to determine whether the test strip 80 is electrically connected to the test meter 10.

Referring to FIG. 4, SPC 308 is connected to switch 310. Switch 310 is connected to the bias driver 312. Bias driver 312 is provided with the DAC signal 312a; current drive 312b and switch signal 312c. The MC 300 provides the DAC signal 312a, which includes analogue voltages in the range 0 to Vref (e.g., about 2.048V). The bias driver 312 can operate in two modes—constant voltage, or constant current. The current-driver line 312b controls the mode of the bias driver 312. Setting the line 312b low converts an op-amp in the bias driver 312 to a voltage follower amplifier. DAC signal 312a output is scaled to Vref/2+/−400 mV full scale. The op-amp in the bias driver outputs this voltage directly to the MC 300 as line driver-line 312d. The voltage of line 312d is generated with respect to the Vref/2 virtual ground. So to drive a suitable bias (e.g., about 20 mV bias), the DAC must drive (through a suitable scaler) about 1.044V. To drive a bias of about +300 mV, the DAC must generally provide about 1.324V, and for the −300 mV bias, the DAC must generally provide about 0.724V. The bias driver circuit 312 also generates the 109 Hz sine wave, which is used for fill detection via capacitance measurement.

On the other hand, if current-drive signal 312a to bias driver 312 is held high, the DAC output is scaled to approximately 0 to approximately 60 mV full scale. Switch signal 312c may also be energized, causing the current path through the test strip to be diverted through a resistor in bias driver 312. The op-amp in bias driver 312 attempts to control the voltage drop across the resistor to be the same as the scaled DAC drive—producing in this case a current of approximately 600 nA. This current is used for sample detection in order to initiate a test measurement.

Bias driver 312 is also connected to a trans-impedance amplifier circuit ("TIA circuit") 314. TIA circuit 314 converts the current flowing though the strip's electrode layer 66a (e.g., palladium) to electrode layer 64a (e.g., gold) contacts into a voltage. The overall gain is controlled by a resistor in TIA circuit 314. Because the strip 80 is a highly capacitive load, normal low-offset amplifiers tend to oscillate. For this reason a low-cost op-amp is provided in the TIA circuit 314 as a unity gain buffer and incorporated within the overall feedback loop. As a functional block, circuit 314 acts as dual op-amp system with both high drive capability and low voltage offset. The TIA circuit 314 also utilizes a virtual ground (or virtual earth) to generate the 1.024V bias on the electrode layer 64a (e.g., gold) contact of the SPC 308. Circuit 314 is also connected to a Vref amplifier circuit 316. This circuit, when in current measuring mode, uses a virtual ground rail set at Vref/2 (approximately 1.024V), allowing both positive and negative currents to be measured. This voltage feeds all of the gain amplifier stage 318. To prevent any circuit loads from 'pulling' this voltage, a unity gain buffer amplifier may be utilized within the Vref amplifier circuit 316.

The strip current signal 314a from the TIA circuit 314 and the virtual ground rail 316a (~Vref/2) from the voltage reference amplifier 316 are scaled up as needed for various stages of the test measurement cycle. In the exemplary embodiment, MC 300 is provided with four channels of amplified signal sensed from the test strip with varying amplifications of the sensed current as need for different stages of the measurement cycle of the test strip during an analyte assay.

In one embodiment, the test meter 10 can apply a test voltage and/or a current between the first contact pad 47 and the second contact pad 43 of the test strip 80. Once the test meter 10 recognizes that the strip 80 has been inserted, the test meter 10 turns on and initiates a fluid detection mode. In one embodiment, the meter attempts to drive a small current (e.g. 0.2 to 1 μA) through the strip 80. When there is no sample present the resistance is greater than several Mega Ohms, so the driving voltage on the op-amp trying to apply the current goes to the rail. When a sample is introduced the resistance drops precipitously and the driving voltage follows. When the driving voltage drops below a predetermined threshold the test sequence is initiated.

Figure 5A:
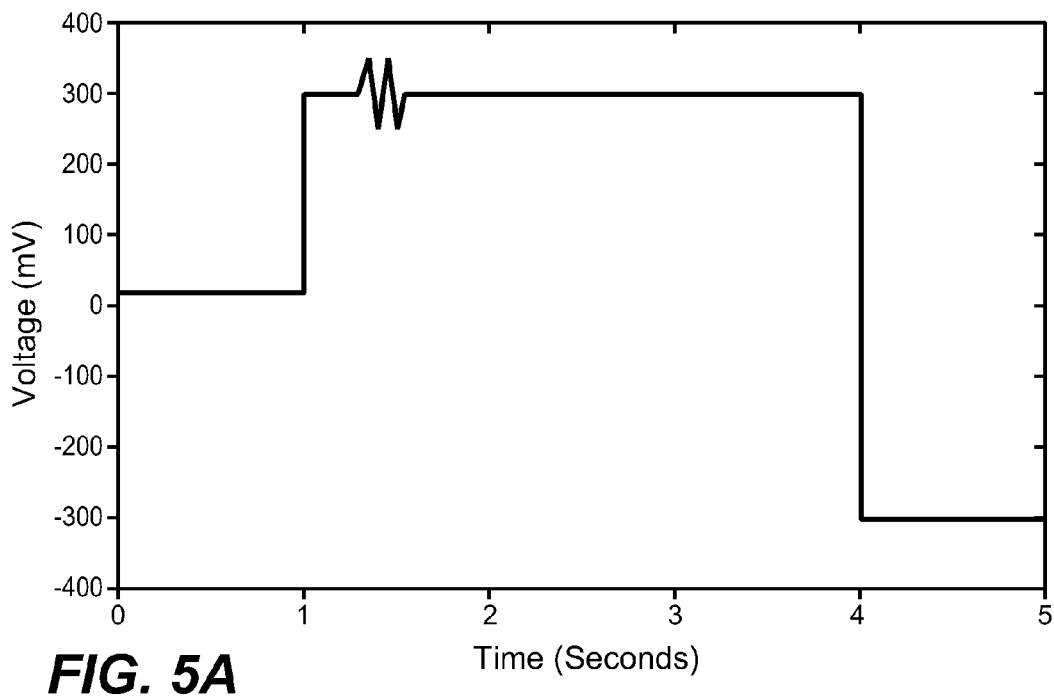
FIG. 5A illustrates the application of voltage over time applied to the test strip.

FIG. 5A shows the voltage to be applied between the electrodes. Time zero is taken to be when the sample detection method has detected that a sample first begins to fill the strip. Note that the sine wave component shown at approximately 1.3 seconds in FIG. 5A is not drawn on the correct timescale for illustration purposes.

After a sample has been detected in the test strip chamber 61, the voltage between the strip electrodes is stepped to a suitable voltage in millivolts of magnitude and maintained for a set amount of time, e.g., about 1 second, then stepped to a higher voltage and held for a fixed amount of time, then a sine wave voltage is applied on top of the DC voltage for a set amount of time, then the DC voltage is applied for a further amount of time, then reversed to a negative voltage and held for a set amount of time. The voltage is then disconnected from the strip. This series of applied voltages generates a current transient such as the one shown in FIG. 5B.

Figure 5B:
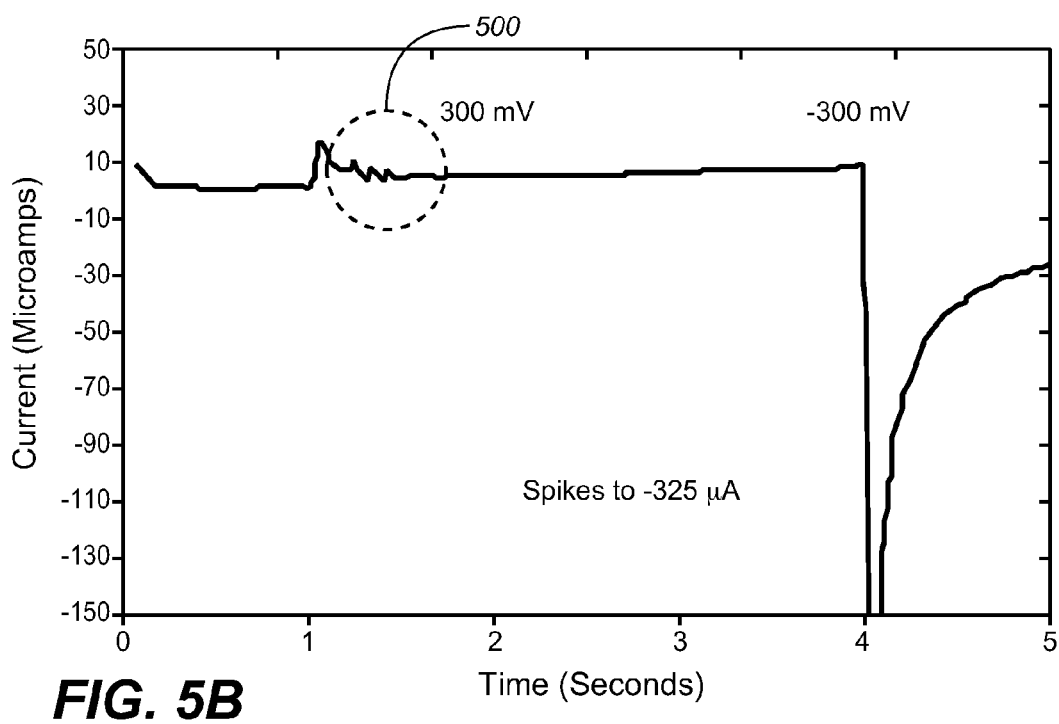
FIG. 5B illustrates the measured current response from the test strip over time.
Figure 7:
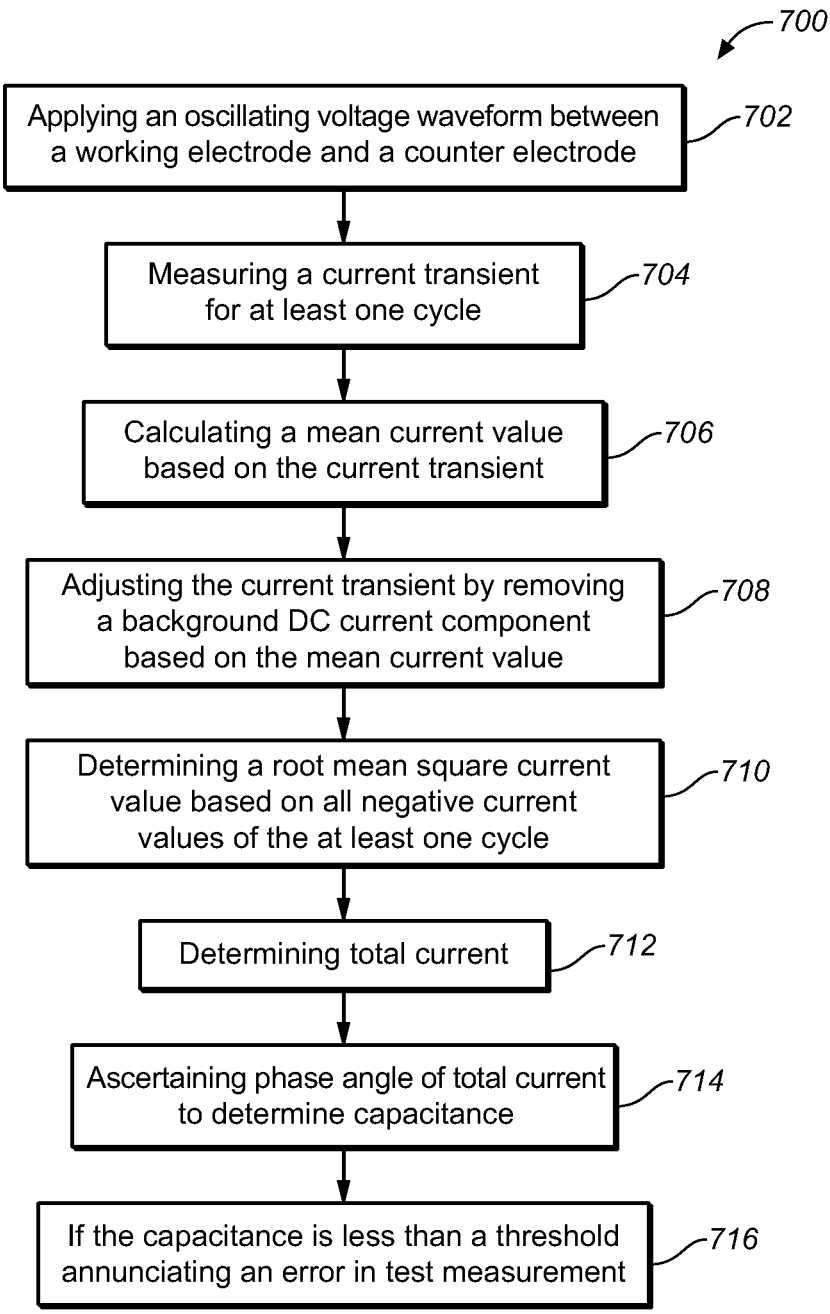
FIG. 7 illustrates an exemplary flow chart of the method to determine capacitance in the exemplary test strip.

In FIG. 5B, the current signal from about 0 to about 1 second (as well as later current samples) may be used for error checking and to distinguish a control solution sample from a blood sample. The signal from about 1 to about 5 seconds is analyzed to obtain a glucose result. The signal during this period is also analyzed for various errors. The signal from about 1.3 to 1.4 seconds is used to detect whether or not the sensor is completely filled with sample. The current from 1.3 to 1.32 seconds, denoted here as trace 500, is sampled at approximately 150 microsecond intervals to determine whether sufficient volume of physiological fluid has filled chamber 61 of the test strip.

In one embodiment for performing a sufficient volume check, a capacitance measurement is used to infer sufficient analyte fill of the chamber 61 of the test strip 80. A magnitude of the capacitance can be proportional to the area of an electrode that has been coated with sample fluid. Once the magnitude of the capacitance is measured, if the value is greater than a threshold and thus the test strip has a sufficient volume of liquid for an accurate measurement, a glucose concentration can be outputted. But if the value is not greater than a threshold, indicating that the test strip has insufficient volume of liquid for an accurate measurement, and then an error message can be outputted.

In one method for measuring capacitance, a test voltage having a constant component and an oscillating component is applied to the test strip. In such an instance, the resulting test current can be mathematically processed, as described in further detail below, to determine a capacitance value.

Figure 9A:
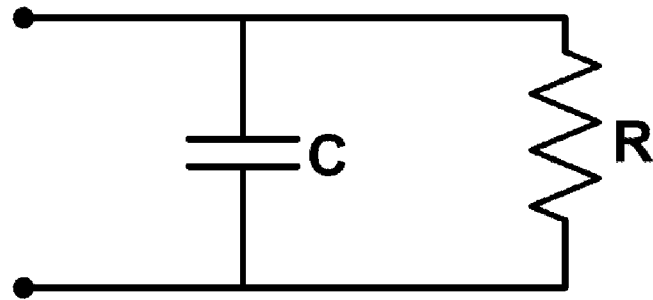
FIGS. 9A and 9B illustrate respectively a model of the test chamber and the equivalent phasor diagram.
Figure 9B:
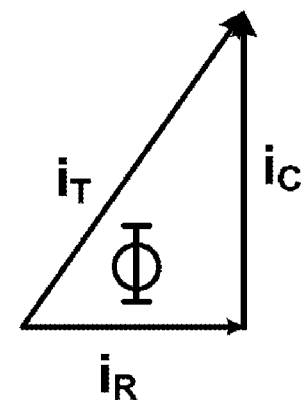

Applicants believe that the biosensor test chamber 61 with the electrode layers can be modeled in the form of a circuit having a parallel resistor and capacitor as shown in FIGS. 9A and 9B.

In this model in FIGS. 9A and 9B, R represents the resistance encountered by the current and C represents a capacitance resulting from the combination of the physiological fluid and reagent electrically coupled to the electrodes. To initiate a determination of capacitance of the chamber, an alternating bias voltage may be applied across the respective electrodes disposed in the chamber, and a current from the chamber is measured. The filling of the chamber 61 is believed to be generally a measure of capacitance only and thus any parasitic resistance, such as, for example, R, must not be included in any determination or calculation of capacitance. Hence, in measuring or sensing the current, any parasitic resistance is believed to affect the measured current. Applicants, however, have discovered a technique to derive capacitance without requiring utilization or knowledge of the resistance through the chamber as modeled above. In order to further explain this technique, a short discussion of the mathematical foundation underlying the technique is warranted.

According to Kirchhoff's Law, total current ($i_T$) through the circuit of FIGS. 9A and 9B is approximately the sum of the current flowing through the resistor ($i_R$) and through the capacitor ($i_C$). When an alternating voltage V (as measured as RMS) is applied, the resistor current ($i_R$) may be expressed as:

$$i_R = V/R \qquad \text{Eq. 1}$$

Capacitor current ($i_C$) can be expressed as:

$$i_C = j\omega CV \qquad \text{Eq. 2}$$

Where:
- j is an imaginary number operator indicating that current leads voltage by about 90 degrees in a capacitor; and
- ω is the angular frequency 2πf where f is frequency in Hertz.

The summation of these components is shown in the phasor diagram of FIGS. 9A and 9B. In the phasor diagram, Φ represents the phase angle of the input as compared to the output. Phase angle Φ is determined by the following trigonometric function:

$$\tan\Phi = I_C / I_R \qquad \text{Eq. 3}$$

By Pythagoras theorem, the square of the total current $i_T$ can be calculated as:

$$i_T^2 = i_C^2 + i_R^2 \qquad \text{Eq. 4}$$

By rearranging Eq. 4 and substituting Eq. 3, the following equation is arrived at:

$$i_C^2 = i_T^2 - i_C^2/(\tan\Phi)^2 \qquad \text{Eq. 5}$$

Resolving for capacitor current $i_C$ and combining with Eq. 2:

$$i_C = \sqrt{(i_T^2 \ast (\tan\Phi)^2/((\tan\Phi)^2+1))} = \omega CV \qquad \text{Eq. 6}$$

Rearranging for C and expanding ω, the capacitance becomes:

$$C = (\sqrt{(i_T^2 \ast (\tan\Phi)^2/((\tan\Phi)^2+1))})/2\pi fV \qquad \text{Eq. 7}$$

Simplification of Eq. 7 leads to:

$$C = |(i_T \sin\Phi)|/2\pi fV \qquad \text{Eq. 8}$$

It can be seen that Eq. 8 does not reference to the resistor current. Consequently, if the system can drive an alternating voltage with frequency f and root-mean-squared ("RMS") amplitude V, and measure total current $i_T$ as RMS value and phase angle Φ, capacitance C of the test chamber 61 can be accurately calculated without having to determine resistance in the biosensor test chamber. This is believed to be of substantial benefit because the resistance of the biosensor strip is difficult to measure, and varies over the 5 second assay time. Resistance is believed to arise from how many charge carriers can flow through the strip for a given electrical bias (voltage), and is therefore reaction dependent. At the 1.3 second point in the assay, the resistance is expected to be anything from 10 kΩ to perhaps 100 kΩ. Hence, by not having to determine the resistance in the biosensor chamber or even the resistance in the measuring circuit, such as a sensor resistor, applicants' invention have advanced the state of the art in improving of the entire test strip.

Implementation of an exemplary technique to determine capacitance C based on Eq. 8 can be understood in relation FIGS. 6A, 6B, 6C, 6D, 6E, and 7. As illustrated in FIG. 5A and step 702 of FIG. 7, an AC test voltage (.±0.50 mV peak-to-peak) of approximately 109 Hz can be applied for 2 cycles during approximately 1-1.3 seconds or at least one cycle indicated in step 704. In the preferred embodiments, the first cycle can be used as a conditioning pulse and the second cycle can be used to determine the capacitance. The alternating test voltage can be of a suitable waveform, such as, for example, a sine wave of approximately 109 Hertz with approximately 50 millivolts peak (FIG. 6C). The sampling can be of any suitable sampling size per cycle, such as, for example approximately 64-65 samples per cycle, shown here in FIG. 6A. Hence, each sample represents approximately 5.6 degrees of the exemplary sine wave.

In FIG. 6A, the system adds a direct-current voltage offset to the alternating current bias and therefore the measured samples in FIG. 6A will also have a direct-current offset, which must be removed via steps 706 and 708 in order to determine the total current $i_T$ according to one example of applicant's technique.

In this technique, a mean of all the 65 samples, referenced here as 602, in FIG. 6A is derived in step 706, which will provide a threshold for the zero current of the a.c. component of the samples. A benefit of this derivation is that the noise across the samples is averaged out. For each sample point, the mean value is subtracted out of each sampled point in step 708, which results in isolating the alternating current component, shown here in FIG. 6B. Thereafter, a RMS value of all the negative values is taken in step 710, to provide for a substantially accurate magnitude of the total current $i_T$. It is noted that the RMS value of the positive values could also be taken, but applicants believe that the positive values are disjointed due to being split across the first and fourth quadrants of the overall cycle, and therefore the negative values are preferred. Once the samples 602 have been manipulated to remove the DC offset, the samples can be plotted to show the output of the current over time, as referenced here at 604 in FIG. 6B.

To determine the phase angle, the system or MC, as appropriately programmed can compare the oscillating input voltage, shown here in FIG. 6C to the oscillating output current to determine the phase angle for step 714. In the preferred embodiments, the sampled data 604 is analyzed to determine a cross-over point from positive to negative current. Because the sampling is based on a discrete number of samples, interpolation can be used to determine substantially when the output current crosses over the zero current line in FIG. 6E, the interpolated cross-over point being referenced here as 608. In the embodiment described here, the phase angle Φ is less than 90 degrees and approximately 87 degrees. For increased accuracy, interpolation can be performed at another cross-over point 610 with approximately 180 degrees subtracted from this second interpolated point 610. The two interpolated values should be within a few degrees and may be averaged out to increase accuracy.

Once the phase angle has been derived, capacitance can be calculated using Eq. 8. In practice, however, it has been determined that the implementation of the trans-impedance amplifier 314 and the gain amplifier introduces additional phase shift into the system. This additional phase shift can be offset by introduction of a compensation value $\Phi_{COMP}$ by measuring the capacitance of the system without a strip in use.

$$C=|i_T \sin(\Phi+\Phi_{COMP})|/2\pi fV \qquad \text{Eq. 9}$$

In the preferred embodiments, the compensation phase angle $\Phi_{COMP}$ ranges from about 5 to about 7 degrees.

Once capacitance of the test strip 80 has been determined, a two-point calibration can be performed to normalize the capacitance value to a value that is independent of any tolerances of the analog components (e.g., resistors, capacitors, op-amps, switches and the like). Briefly, the two-point calibration is performed by: placing a 550 nF capacitor with 30 k parallel resistance across the measurement input; command the meter to measure the capacitance, and note the value produced; place a 800 nF capacitor with 30 k parallel resistance across the measurement input; command the meter to measure the capacitance, and note the value produced. These two points will give an indication of the gain and offset of the measurement capability of that particular hardware instance (not the design). A slope and offset are then calculated from the measurement errors, and stored in the meter's memory. The meter is now calibrated.
When a strip is inserted and a sample applied, the capacitance is measured and the stored slope and offset are applied to correct the measurement.

After completion of the device calibration, an evaluation is made to determine whether the test chamber 61 has been sufficiently filled with test fluid. The evaluation can be based on a capacitance magnitude of at least 65% to 85% of an average capacitance value derived from a large sample of good filled test strips.

To test the robustness of this exemplary technique, applicants intentionally introduced noise into the system to determine the percent error as compared to referential parallel R-C circuit. In Table 2 below, despite the number of Analog-to-Digital-Converter ("ADC") noise counts were introduced, error relating to current, phase angle and capacitance were less than 1%.

TABLE 2

| ADC Noise Counts | Current Error (%) | Phase Angle Error (%) | Capacitance Error (%) |
| --- | --- | --- | --- |
| ±1 | −0.05 | −0.1 | −0.09 |
| ±2 | −0.08 | −0.19 | −0.21 |
| ±3 | 0.2 | −0.34 | −0.34 |
| ±4 | 0.21 | 0.39 | 0.37 |

Figure 8A:
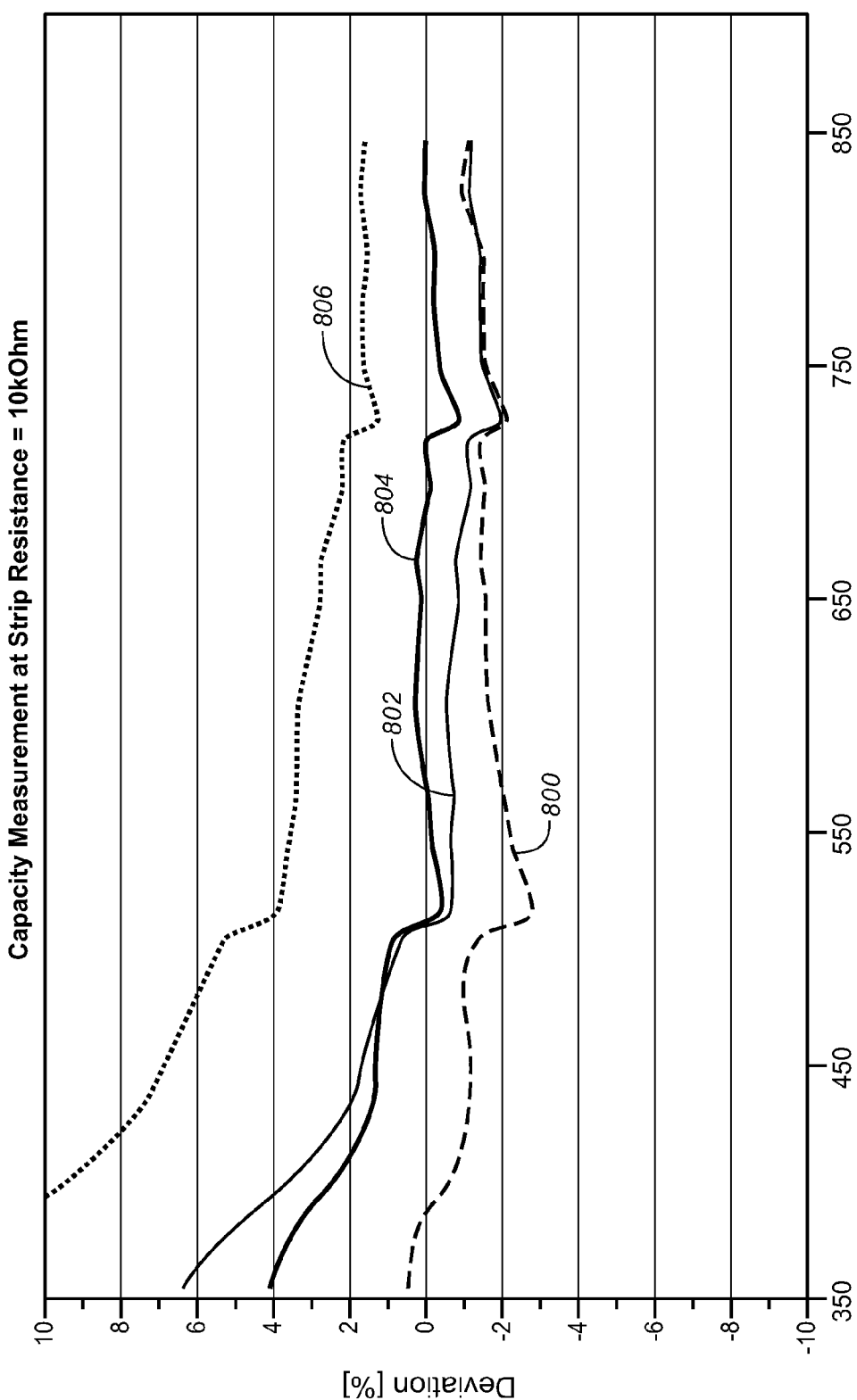
FIG. 8A illustrates the percent error of the exemplary embodiments versus a known system and other related techniques of the applicants.
Figure 8B:
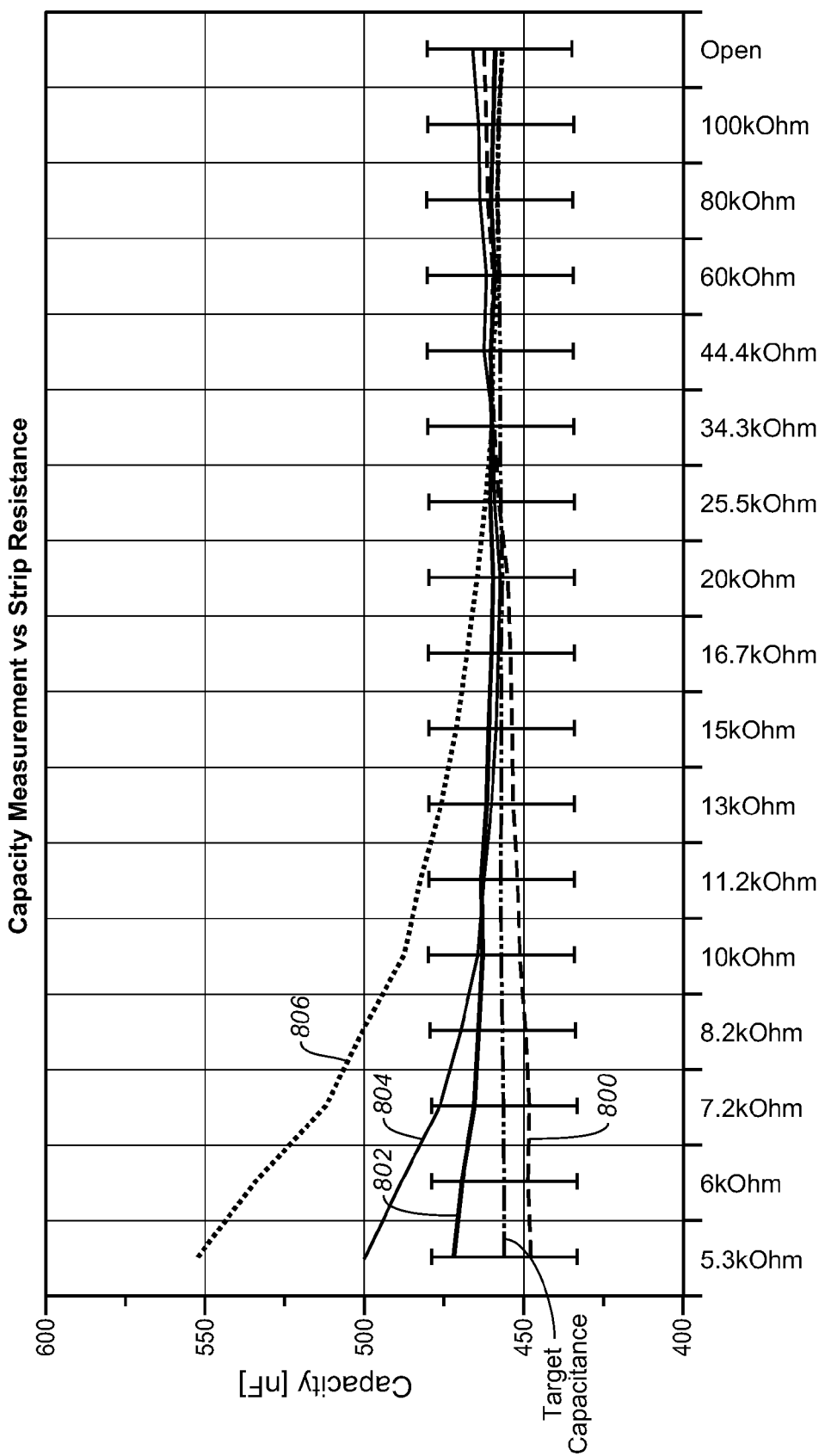
FIG. 8B illustrates the distribution of capacitance of respective capacitance measurement techniques over the range of resistance in the exemplary test strip.

Comparison of the exemplary techniques with other techniques confirms the increased accuracy of applicants' technique. For example, in FIG. 8A, capacitance is measured from a sample of strips in the range of about 350 to about 800 nanoFarad. A fully filled strip has capacitance ranging between 600 and 700 nF depending on whether control solution or blood is used. Partially filled strips exhibit lower capacitance of course. The capacitance is measured with the subject embodiment to determine percent deviation from a referential parallel R-C circuit. The percentage error is calculated by having several "golden" R-C combinations that have been calibrated using a commercially available LCR meter. These R-C combinations (which have been found as generally error-free exemplars and therefore are "golden") are presented to the strip connector in turn, and the system is commanded to read the capacitance. This test is repeated using several other samples of the system to determine the precision and reliability of the measurement technique. Reference curve 800 represents the exemplary technique with error rate from the referential datum of less than 3% through the capacitance range of about 350 nanoFarad to about 850 nanoFarads. In contrast, capacitance measurement in an existing meter system available from LifeScan Inc., in the Netherlands shows error curve 806 ranging from less than 2 percent to greater than 10 percent through this range of capacitance. Applicants' related capacitance measurement techniques 802 and 804 fall in between the upper boundary 806 sets by the existing analyte measurement system and the lower boundary 800 sets by the exemplary technique.

Although the exemplary embodiments, methods, and system have been described in relation to a blood glucose strip, the principles described herein are also applicable to any analyte measurement strips that utilize a physiological fluid on a reagent disposed between at least two electrodes.

As noted earlier, the microcontroller can be programmed to generally carry out the steps of various processes described herein. The microcontroller can be part of a particular device, such as, for example, a glucose meter, an insulin pen, an insulin pump, a server, a mobile phone, personal computer, or mobile hand held device. Furthermore, the various methods described herein can be used to generate software codes using off-the-shelf software development tools such as, for example, C or variants of C such as, for example, C+, C++, or C-Sharp. The methods, however, may be transformed into other software languages depending on the requirements and the availability of new software languages for coding the methods. Additionally, the various methods described, once transformed into suitable software codes, may be embodied in any computer-readable storage medium that, when executed by a suitable microcontroller or computer, are operable to carry out the steps described in these methods along with any other necessary steps.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of determining capacitance of a biosensor chamber having two electrodes disposed in the chamber and coupled to a microcontroller, the method comprising:
   initiating an electrochemical reaction in the biosensor chamber;
   applying an oscillating voltage of a predetermined frequency to the chamber;
   determining a phase angle between a current output and the oscillating voltage from the chamber; and
   calculating a capacitance of the chamber based on a product of the current output and a sine of the phase angle divided by a product of two times pi times the frequency and the voltage, and wherein the calculating comprises calculating capacitance with an equation of the form:

$$C = |(i_T \sin \Phi)| \div 2\pi f V$$

where:
   $C \approx$ capacitance;
   $i_T \approx$ total current;
   $\Phi \approx$ phase angle between total current and resistor current;
   $f \approx$ frequency; and
   $V \approx$ voltage
   and in which the calculating further comprises:
   sampling a plurality of current outputs from the chamber over one cycle of the frequency;
   obtaining a mean of sampled current output;
   subtracting the mean from each sampled current of the plurality of current outputs; and
   extracting root-mean-squared value of all negative values from the subtracting to provide for the total current output.

2. The method of claim 1, in which the calculating comprises:
   determining from the sampling, at least one cross-over point of the current from negative to positive values; and
   interpolating proximate the at least one cross-over point of the current to determine a first angle at which the current changes from positive to negative or negative to positive.

3. The method of claim 2, in which the interpolating the at least one cross-over point of the current comprises:
   interpolating another cross-over point from the sampling to determine another angle at which the current changes from positive to negative or negative to positive; and
   subtracting from the another angle approximately 180 degrees to provide for a second angle.

4. The method of claim 3, in which the subtracting further comprises calculating an average of the first and second angles.

5. The method of claim 3, in which the calculating comprises determining a difference in the angle between the oscillating input current and the output current as the phase angle.

* * * * *